United States Patent [19]

Stabinger et al.

[11] Patent Number: 5,339,258

[45] Date of Patent: Aug. 16, 1994

[54] APPARATUS FOR DETERMINING THE DENSITY OF LIQUIDS AND GASES FROM A PERIOD OF AN OSCILLATOR FILLED WITH A TEST SAMPLE

[76] Inventors: Hans Stabinger, Peterstalstr, 156, A-8042 Graz; Hans Leopold, Sonnleitenweg 17, A-8043 Graz; Helmut Heimel, Hugo-Schuchardtstr. 34, A-8010 Graz, all of Austria

[21] Appl. No.: 877,891

[22] Filed: May 1, 1992

[51] Int. Cl.$^5$ .............................. G01N 9/00
[52] U.S. Cl. .................... 364/558; 73/32 R; 73/32 A
[58] Field of Search ............ 73/32 R, 54.01, 32 A; 364/556, 558

[56] References Cited

U.S. PATENT DOCUMENTS

| | | | |
|---|---|---|---|
| 3,339,400 | 9/1967 | Banks | 73/32 A |
| 3,385,104 | 5/1968 | Banks | 73/32 A X |
| 3,910,101 | 10/1975 | Kratky et al. | 73/32 A |
| 4,524,610 | 6/1985 | Fitzgerald et al. | 73/54 |
| 4,602,498 | 7/1986 | Glikberg et al. | 73/32 A |
| 4,838,084 | 6/1989 | Leopold | 73/32 A |
| 4,926,682 | 5/1990 | Holm-Kennedy et al. | 73/54.01 |
| 5,005,400 | 4/1991 | Lew | 73/32 A |
| 5,237,853 | 8/1993 | Cassaday et al. | 73/32 A |
| 5,253,533 | 10/1993 | Lam et al. | 73/861.37 |

FOREIGN PATENT DOCUMENTS

| | | |
|---|---|---|
| 331539 | 8/1976 | Austria . |
| 356943 | 6/1980 | Austria . |
| 222503 | 5/1987 | European Pat. Off. . |
| 1498548 | 7/1964 | Fed. Rep. of Germany . |
| 2208525 | 6/1974 | France . |
| 2001761 | 2/1979 | United Kingdom . |
| 2187286 | 9/1987 | United Kingdom . |
| 2236591 | 4/1991 | United Kingdom . |
| 9012306 | 10/1990 | World Int. Prop. O. . |

OTHER PUBLICATIONS

Langdon, R. M., "Vibratory Process Control Transducers", The Marconi Review, vol. XLIII (1980), No. 218, Rugby, Great Britain, pp. 156–175.

*Primary Examiner*—Edward R. Cosimano
*Attorney, Agent, or Firm*—Cushman, Darby & Cushman

[57] ABSTRACT

A device for determining the density of liquids and gases uses an actuator to physically excite a sample of the material being tested. The oscillations induced by this excitation are detected by a sensor and amplified by an oscillation amplifier, and the amplified signal is used to drive the actuator in a closed-loop fashion. To compensate for errors in the density measurement process arising from non-ideal viscous effects of the sample, a phase change circuit or inverter may be shunted into the amplifier circuit to change the phase of the excitation signal. By observing the effects of the excitation phase change on the oscillation frequency of the sample, the sample's viscosity can be measured, and the system can compensate for its effects.

10 Claims, 6 Drawing Sheets

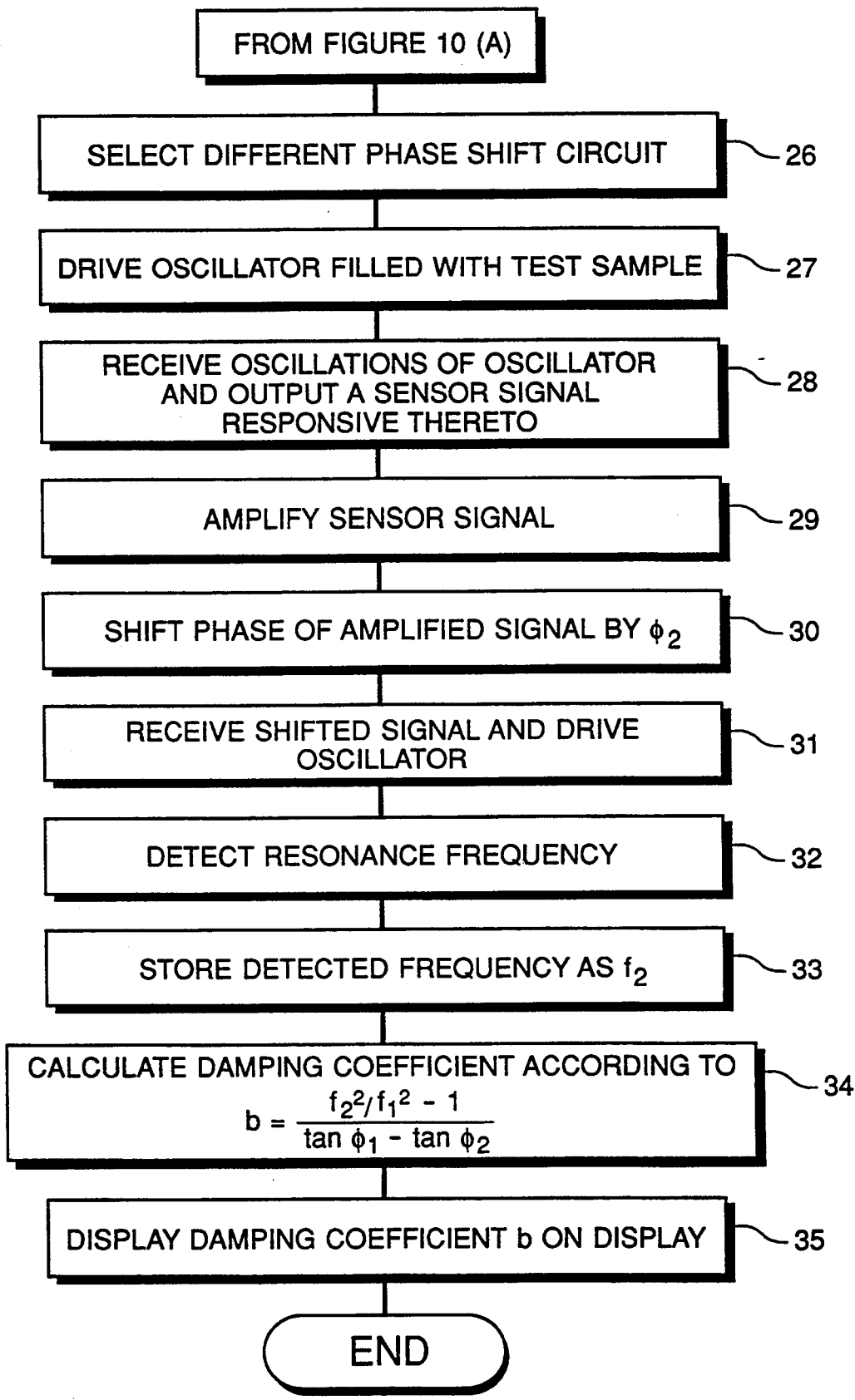

APPARATUS FOR DETERMINING THE DENSITY OF LIQUIDS AND GASES FROM A PERIOD OF AN OSCILLATOR FILLED WITH A TEST SAMPLE

BACKGROUND OF THE INVENTION

1. Field of the Invention

This invention relates to an apparatus for determining the density of a liquid or a gas. The apparatus has an oscillator body filled with a test sample of the liquid or gas being measured. A sensor outputs signals representative of oscillations of the oscillator body which are amplified by an oscillation amplifier. The amplifier signals are supplied to a actuator disposed on the output side of the oscillation amplifier to drive the oscillator.

2. Description of the Related Art

Such an apparatus was disclosed, for example, in Austrian Letters Patent 331,539. In this apparatus a circuit for excitation and detuning is provided. The circuit essentially consists of an amplifier and a limiter as well as a further circuit for the temperature-dependent de-tuning of the resonance frequency of the oscillator.

The latter consists of a temperature-dependent resistance bridge, a summing amplifier and integrators for phase shifting.

Thus, it is possible with this known device to obtain the excitation of the oscillating body and de-tuning of the resonance frequency, by means of which a temperature compensation and/or a counter mass compensation can be achieved, the latter in order to reduce a "counter mass—spring—measuring oscillator" model of a coupling oscillator system, which is the basis for calculating the density, to the theoretically ideal, simple "spring—oscillating mass" oscillator system.

The oscillator with the sample to be tested contained in it represents an oscillating body which is embodied in such a way that a defined volume of the test sample to be tested takes part in the oscillation and thus affects the period length $\tau$. In this case the period length $\tau$ of such an oscillating body can be calculated in accordance with equation (1):

$$\tau = 2\pi \sqrt{\frac{M_o + \rho V}{c}} \quad (1)$$

where $M_o$ is the mass of the empty oscillator, c its resilient constant, $\rho$ the density and V the volume of the test sample participating in the oscillation. The quotients $M_o/c$ and $V/c$ can be considered to be oscillation-specific apparatus constants.

Following transformation and definition of simple constants A and $T_o$, the following equation (2) is obtained:

$$\rho = \frac{1}{A} \cdot (T^2 - T_o^2) \quad (2)$$

where T is a whole number multiple of the period length $\tau$, $T_o$ is a multiple of the period length $\tau_o$ of the empty oscillator, increased by the same factor. The factors A and $T_o$ are calculated by setting the equation (2) for two known values of $\rho$ and T and solving in accordance with the factors A and $T_o$.

If the oscillating body, as in the known solution, consists of an oscillating tube, clamped on one or both ends, in which the substance to be measured is enclosed, the equations (1) and (2) are only valid for non-viscous liquids. A larger period is observed with viscous liquids of a defined density.

SUMMARY OF THE INVENTION

It is the object of the invention to disclose an apparatus of the previously mentioned type which allows to correct for the effects of the viscosity of the sample to be tested.

This is attained in accordance with the invention in that at least one circuit is provided which can be switched into the oscillation amplifier by means of a change-over switch and which causes a phase shift.

In this way it is possible to excite the oscillator with signals phase-shifted with respect to its own oscillations.

If an oscillating body is excited by a sinusiodal force in phase with its velocity amplitude, the natural resonance frequency occurs because the velocity-dependent damping force is completely cancelled by the exciter force. However, if the phase of the excitation force does not agree with that of the velocity amplitude, the result is a resonance frequency of the oscillating body which differs from the natural by an amount which is approximately proportional to the size of the damping force and the phase difference between the excitation and the damping force.

The result of this is that the damping force can be calculated from the de-tuning of the oscillating body which results when the oscillating body is successively excited by excitation forces of different phases.

Thus it is possible by means of the apparatus of the invention to excite the oscillator containing the sample to be tested with signals of different phase positions so that two resonance frequencies result which are detected and from which the damping constant can be calculated in accordance with equation (3):

$$b = \frac{f_2^2/f_1^2 - 1}{\tan\phi_1 \tan\phi_2} \quad (3)$$

where b is the damping constant, $f_1$ and $f_2$ are the resonance frequencies, $\phi_1$ and $\phi_2$ are the associated phase differences between the exciter signals and the movement of the oscillator.

It is possible to determine experimentally the dependency of the relative measurement error of the density $\Delta\rho/\rho$, caused by the viscosity, with respect to the damping constant b. For this purpose, test samples of different viscosity and known density can be placed into the oscillating body and the two resonance frequencies can be measured. From this, it is possible to calculate the viscosity-dependent density measuring error $\Delta\rho/\rho$ and the associated damping constant b for every test sample.

In accordance with a further characteristic of the invention it can be provided that at least two frequency measuring and memory circuits are connected with the oscillator amplifier.

The resonance frequencies can be simply measured and stored in this way and can be called up from these circuits for further processing.

It can further be provided that the two change-over switches are controlled by a microprocessor which is connected with the frequency measuring and memory circuits and preferably with a density display.

In this way, there is the opportunity for a simple and rapid evaluation of the measurements.

In accordance with a further characteristic of the invention, it can be provided that at least two transducers which are at a distance from each other in the axial direction of the oscillator are provided for generating oscillations of zero and higher order modes.

Because of the higher resonance frequencies, oscillations of higher order result in a larger effect on viscosity in a broader range in which monotonically rising damping is a function of viscosity, than does the oscillation of zero-order mode. This means that the higher order oscillations are advantageously used for determining the effect of viscosity on the density measurement, while zero order mode oscillations, because of their minimal viscosity-dependent density measuring errors, are advantageously used for density measuring.

It can furthermore be provided that a microprocessor-controlled inverter is provided in the oscillation amplifier, by means of which the phase position can be rotated by 180°.

In this way, control of the actuators is assured in a simple manner, by means of which the oscillation of the oscillator is maintained in at least two modes of oscillations. In this connection, it can be further provided that the switchable inverter is formed by parallel connection of a follower and an inverter at their inputs, the outputs of which can be connected with the two change-over switches via a change-over contact controlled by the microprocessor.

It can be provided in accordance with another characteristic of the invention that the inverter is formed by an operational amplifier connected as an inverter, the non-inverting input of which is connected with the input of the inverter stage via a resistor and can be selectively connected or disconnected with ground via a microprocessor-controlled switch, where the output of this inverter can be connected with the two change-over switches.

This step results in a structurally very simple solution.

The invention will be described in detail below by means of the drawings.

DETAILED DESCRIPTION OF THE PRESENTLY PREFERRED EXEMPLARY EMBODIMENTS

Figure 1:
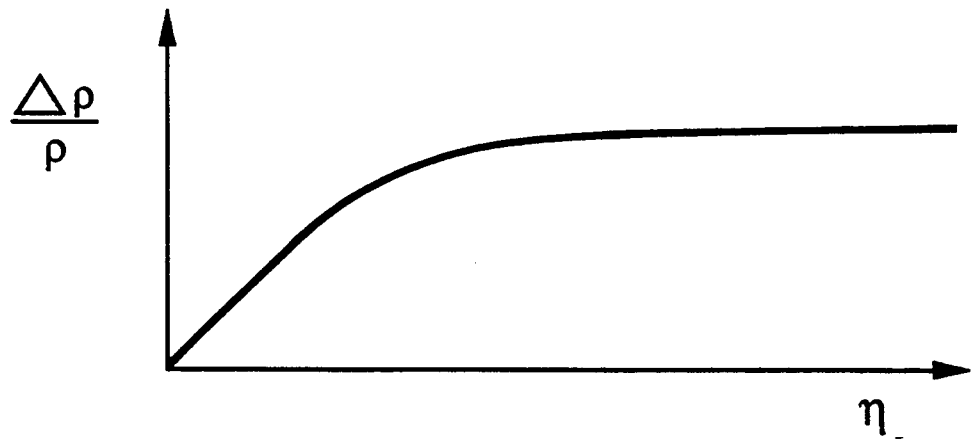
FIG. 1 is a diagram of the density measuring error $\Delta\rho/\rho$ as a function of the viscosity during excitation in the zero order mode oscillation.

It can be seen from FIG. 1 that when measuring the density in the zero order mode oscillation, the density measuring error $\Delta\rho/\rho$ first essentially rises linearly with rising viscosity $\eta$ and then makes a transition in the shape of a curve into a saturation range in which the density measuring error now only rises a little with continued increases in viscosity of the sample to be tested.

Figure 2:
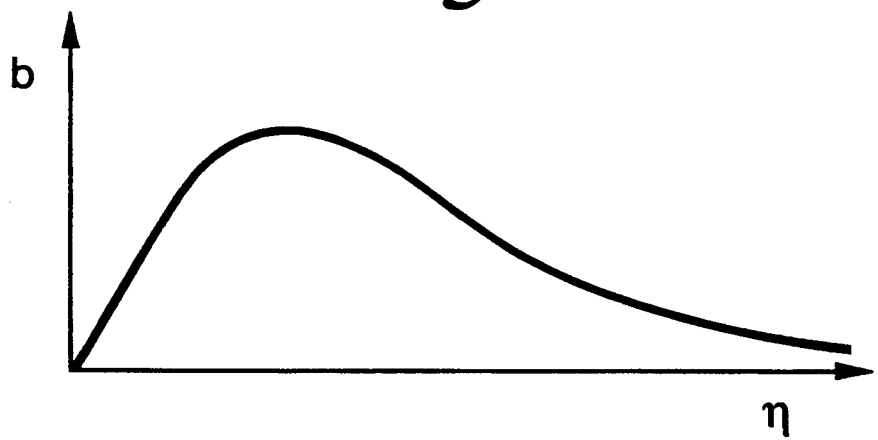
FIG. 2 is a diagram of the damping constant b as a function of the viscosity during excitation in the zero order mode oscillation.

FIG. 2 shows the course of the damping constant b in the zero order mode oscillation as a function of the viscosity $\eta$. It can be seen from this diagram that in the area of low viscosity the damping constant rises relatively steeply with increasing viscosity and, following a transition area, falls relatively slowly.

Figure 3:
FIG. 3 is a diagram combining the diagrams of FIGS. 1 and 2.

FIG. 3 shows the diagram, resulting from a combination of the two diagrams in accordance with FIGS. 1 and 2, of the density measuring error $\Delta\rho/\rho$ as a function of the damping constant b. In this case, it can be seen that the relationship between the density measuring error and the damping constant is ambiguous, which must be attributed to the reduction of damping at high viscosity. By means of the measurement of the viscosity effect in the first or higher order mode oscillations, it is possible to push the area of ambiguity from the area of the technically important liquids to higher viscosities (see FIG. 7).

Figure 4:
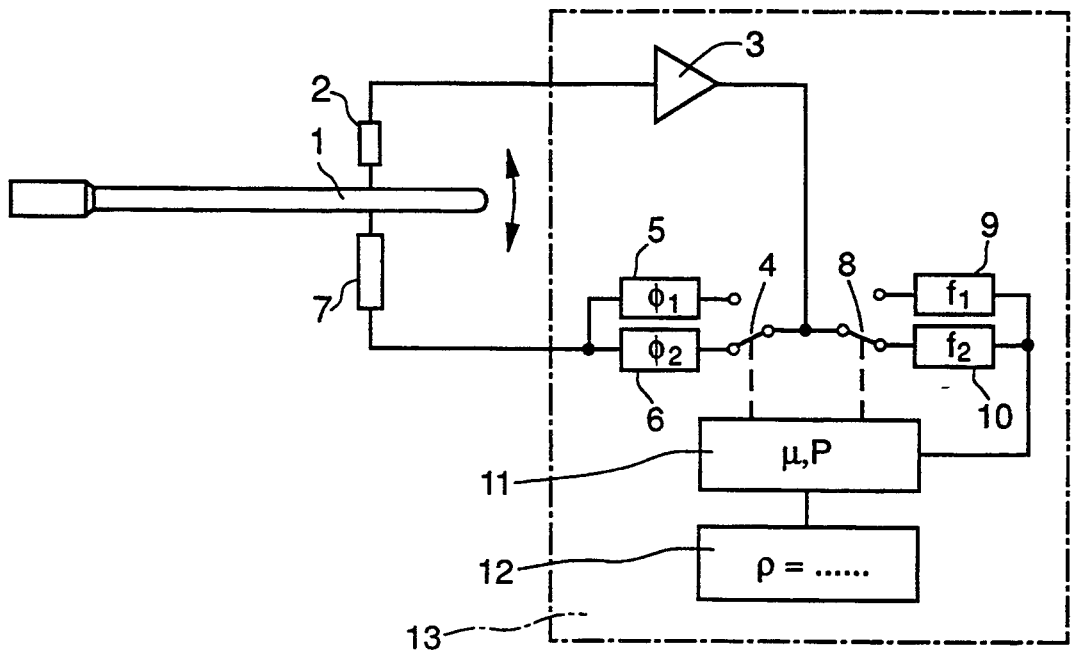
FIG. 4 is a first embodiment of an apparatus in accordance with the invention.

FIG. 4 schematically shows an apparatus in accordance with the invention. In this case, the oscillator 1, which can be filled with a sample of liquid or gas to be tested, can be brought to oscillate by means of a actuator 7 (Step 19 in FIG. 19A and Step 27 in FIG. 10B). In this case the actuator 7 transforms electrical signals into forces which excite the oscillator.

Figure 10:
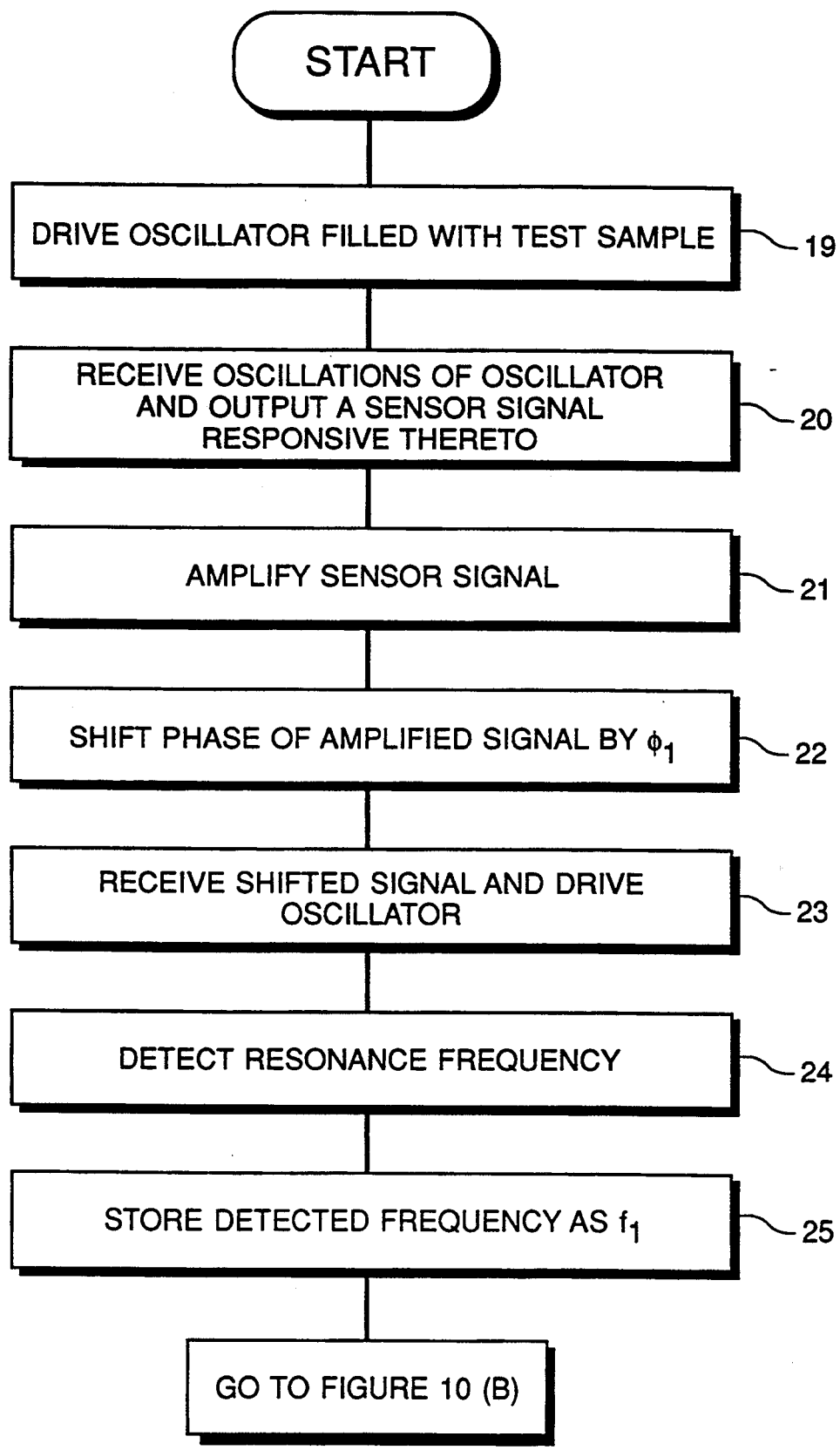
FIGS. 10A and 10B are a flowchart of the operation of the first embodiment of the invention.

The oscillations of the oscillator 1 are detected by a sensor 2 and transformed by it into electrical signals (FIG. 10A, Step 20; FIG. 10B, Step 28) which are supplied to an amplifier 3 of the oscillation amplifier 13. The amplified signals (FIG. 10A, Step 21; FIG. 10B, Step 29) reach the inputs of two reversing switches 4 and 8.

In the embodiment illustrated, the reversing switch 4 switches selectively to one of two circuits 5, 6, which are connected in parallel to each other and are connected at their outputs with the actuator 7. These circuits 5, 6 cause a phase shift (FIG. 10A, Step 22; FIG. 10B, Step 30) of the signals provided to the actuator 7 (FIG 10A, Step 23; FIG. 10B, Step 31) with respect to the oscillations of the oscillator 1 or to the output signals of the sensor 2. The amount of the phase shift caused by the circuit 5 is different from that caused by the circuit 6. These circuits can be constituted by low-pass filters, for example.

Switching from one circuit 5, 6 to the other (FIG. 10B, Step 26) results in different resonance frequencies of the oscillator 1 which are detected and stored by the frequency measuring and memory circuits 9, 10 connected to the reversing switch 8. The resonance frequency occurring when one of the circuits 5, 6 is switched on is detected (FIG. 10A, Step 24; FIG. 10B, Step 32) and stored (FIG. 10A, Step 25; FIG. 10B, Step 33) in one of these circuits 9, 10, and the resonance frequency occurring when the second circuit 5, 6 is switched on is detected and stored in the second circuit 9, 10.

Control of the two reversing switches 4, 8 is provided by a microprocessor 11 which is connected with the outputs of the frequency measuring and memory circuits 9, 10.

This microprocessor 11 evaluates the values detected or stored in the circuits 9, 10 in accordance with the equations (1), (2) and (3) and calculates the density of the tested sample (FIG. 10B, Step 34). This is displayed on the density display 12, which is connected to the microprocessor 11 (FIG. 10B, Step 35).

Figure 5:
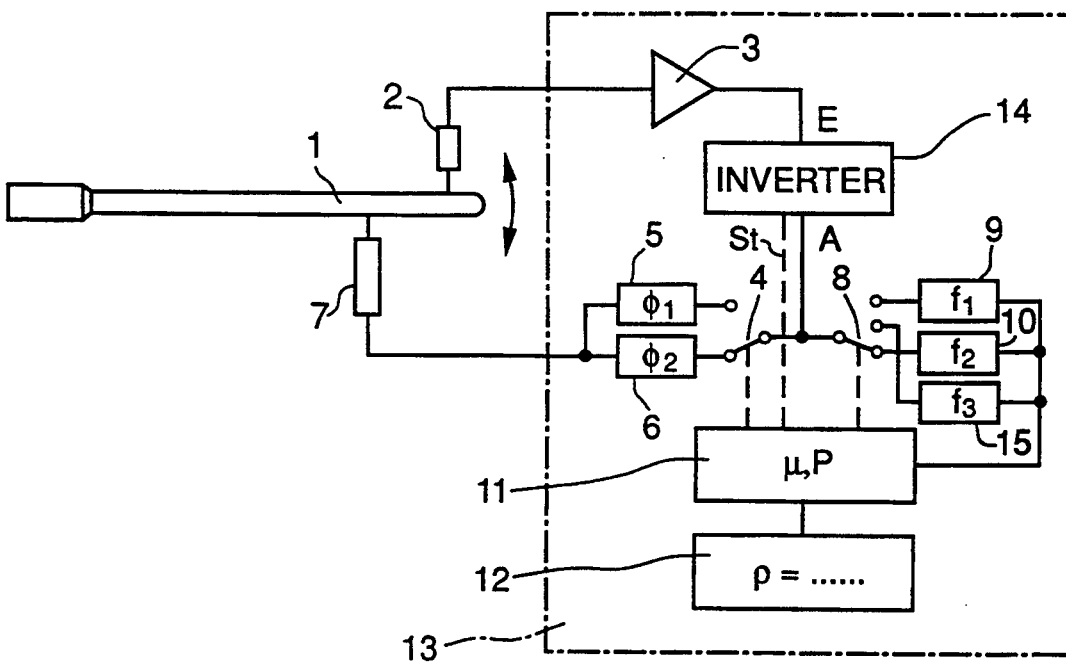
FIG. 5 is a further embodiment of an apparatus in accordance with the invention where the zero order mode oscillation and the first order mode can be excited.

The embodiment of the apparatus in accordance with the invention of FIG. 5 differs from that of FIG. 4 in that two transducers 2, 7, which are at a distance from each other in the axial direction of the oscillator 1 are provided, by means of which the oscillator can be excited in the zero order oscillation mode as well as in the first order mode, depending on the position of the switchable inverter 14.

For this purpose a switchable inverter 14, controlled by the microprocessor 11, is inserted between the amplifier 3 and the two reversing switches 4 and 8 and is used for conditionally reversing the phase position by 180°. Furthermore, an additional circuit 15 is provided which can be switched by means of the reversing switch 8 and measures a frequency $f_3$.

By means of the device in accordance with FIG. 5 it is possible to excite the oscillator 1 in the zero order oscillation mode in the phase position $\phi_1$, in the first order in the phase position $\phi_1$ and in the first order in the phase position $\phi_2$. These modes correspond to the frequencies $f_1$, $f_2$ and $f_3$, which are detected and stored by the frequency measuring and memory circuits 9, 10 and 15.

The damping constant b in the oscillation of the first order results from equation (4):

$$b = \frac{f_3^2/f_2^2\ 1}{\tan\phi_1 - \tan\phi_2} \quad (4)$$

The density of the liquid is calculated from the frequency $f_1$ in accordance with equation (2). In an advantageous manner the damping constant b is measured following the zero order mode of oscillation measurement in time, in that the inverter 14 is switched into the first order mode and the frequencies $f_2$ and $f_3$ are detected via the two phase shift circuits 5, 6. A relationship is developed from the experimentally observed relative density measuring error $\Delta\rho/\rho$ and the associated damping constant b, which allows the correction of the density error in a measurement of viscous liquids.

Figure 8:
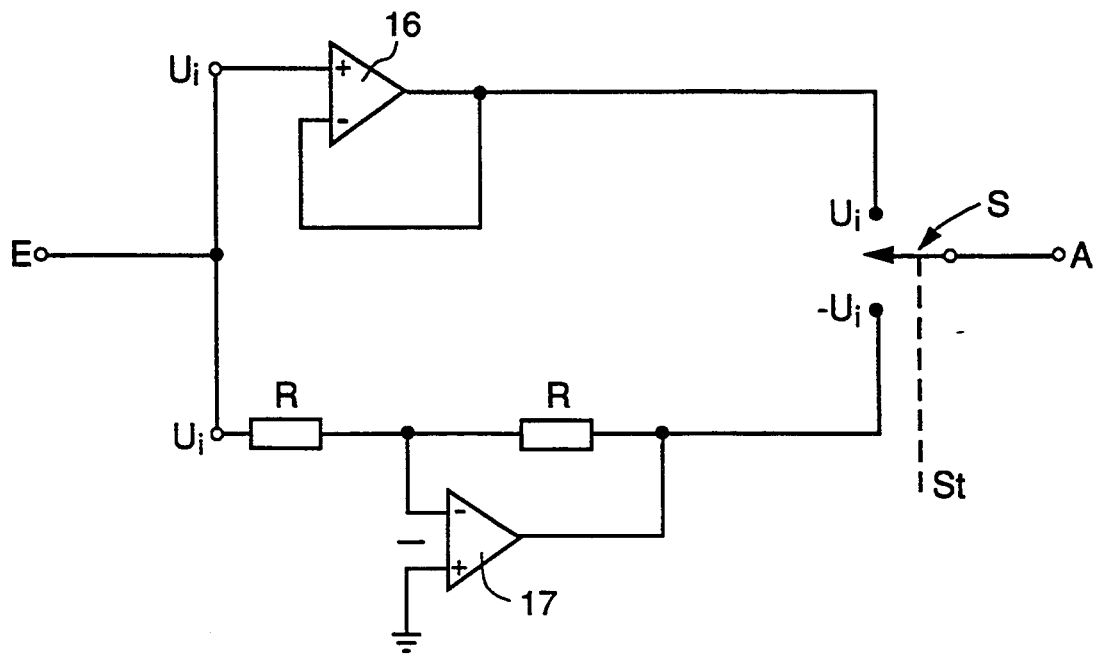
FIGS. 8 and 9 are embodiments of a switchable inverter.
Figure 9:
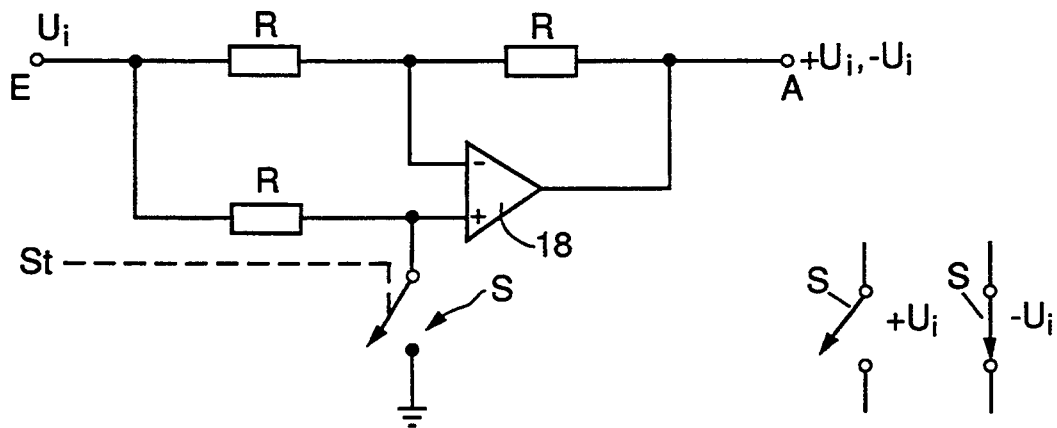

FIGS. 8 and 9 show variant embodiments of a switchable inverter 14. In the embodiment in accordance with FIG. 8, the inverter consists of two operational amplifiers 16, 17 connected in parallel at their inputs, the former being connected as a follower, the latter as an inverter.

Depending on the position of a switch S controlled by the microprocessor 11, the non-inverted or the inverted input voltage is delivered at the output A of the switchable inverter 14. As shown in FIG. 5, the output A of the switchable inverter 14 is connected with the two reversing switches 4, 8.

With the embodiment in accordance with FIG. 9, only one operational amplifier 18, connected as an inverter, is provided, and its non-inverting input is connected to the input E along with a resistor. The non-inverting input E can be connected to or disconnected from a fixed potential (ground) via the switch S controlled by the microprocessor 11. Because of this, the non-inverted or inverted input voltage appears at the output A, depending on the position of the switch S.

Figure 6:
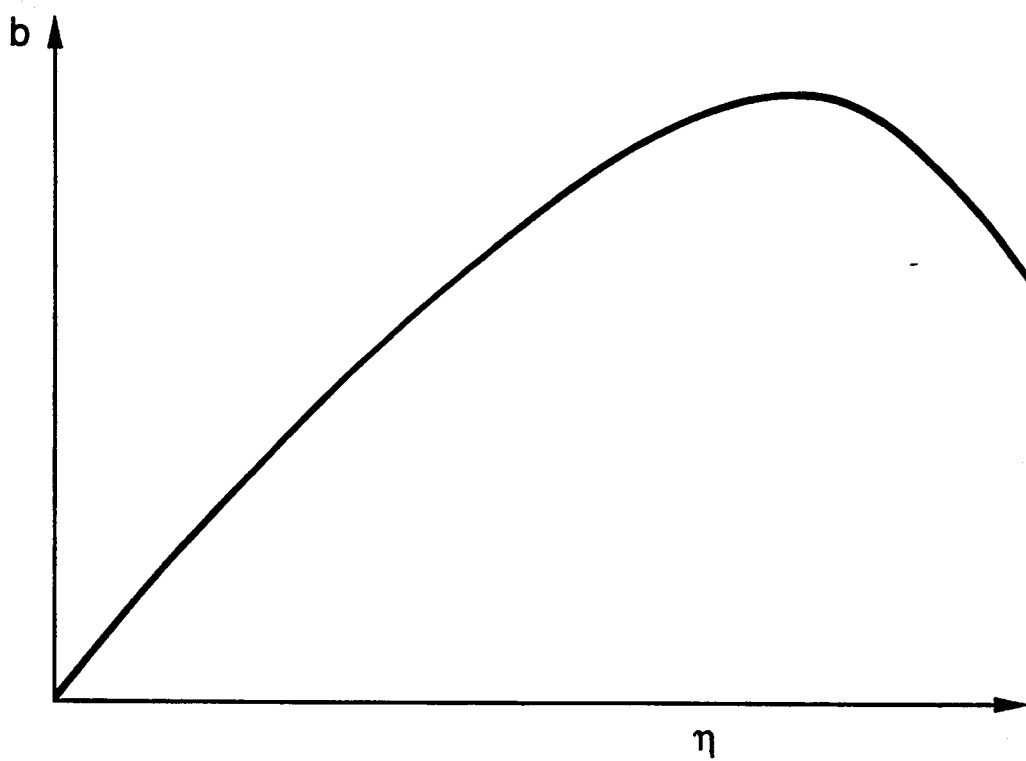
FIG. 6 is a diagram of the damping constant b as a function of viscosity during excitation in the first order mode oscillation.

As can be seen from the diagram of FIG. 6, in which the course of the damping constant b is shown as a function of the viscosity $\eta$, when the oscillator 1 is excited to an oscillation of the first order, a considerably larger range of viscosity results, in which the damping constant b increases monotonically and therefore can be employed for measuring, than results with the excitation to an oscillation of zero order.

Figure 7:
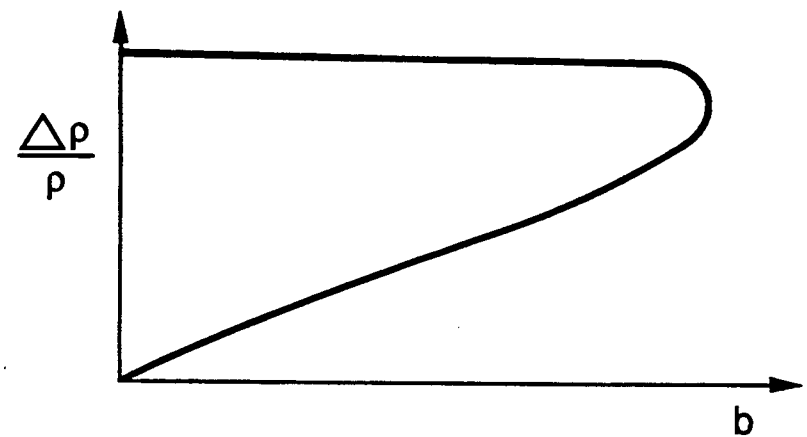
FIG. 7 is a diagram of the density measuring error as a function of the damping constant b as it follows from the combination of the diagrams according to FIGS. 1 and 6.

Also, as can be seen in FIG. 7, the result is a considerably larger range of viscosity correction.

What is claimed is:

1. An apparatus for determining liquid and gas density, said apparatus comprising:
    an oscillator filled with a test sample;
    a sensor for detecting oscillations of said oscillator and outputting a sensor signal responsive to said detected oscillations;
    an oscillation amplifier for amplifying said sensor signal and providing said amplified signal at an output;
    a actuator for receiving said amplified signal and driving said oscillator;
    at least one phase shifting circuit;
    at least one change-over switch for selectively connecting said at least one phase shifting circuit to said oscillation amplifier to cause a phase shift of said amplified signal; and
    determining means responsive to said sensor signal for determining the density of said test sample.

2. The apparatus of claim 1, said determining means further comprising:
    a microprocessor for controlling said at least one change-over switch;
    wherein said microprocessor is connected with said at least one phase shifting circuit.

3. The apparatus of claim 2, wherein said microprocessor is connected to a density display.

4. The apparatus of claim 1, said at least one phase shifting circuit comprising:
    at least two frequency measuring and memory circuits.

5. The apparatus of claim 4, said determining means further comprising:
    a microprocessor for controlling said at least one change-over switch;
    wherein said microprocessor is connected with said frequency measuring and memory circuits.

6. The apparatus of claim 5, wherein said microprocessor is connected to a density display.

7. The apparatus of claim 1, further comprising:
    at least two transducers for generating oscillations of zero and higher order modes;
    wherein said transducers are disposed at a distance from each other in an axial direction of the oscillator.

8. The apparatus of claim 7, said oscillation amplifier comprising:
    a microprocessor-controlled inverter for selectively shifting the phase of said amplified signal by 180°.

9. The apparatus of claim 8, said inverter comprising:
    a follower and inverter parallel-connected at their inputs;
    a change-over contact having inputs connected to the output of said follower and to the output of said inverter and having outputs connected to said at least one reversing switch;
wherein said change-over contact is controlled by said microprocessor.

10. The apparatus of claim 8, said inverter further comprising:
an operational amplifier connected as an inverter;
wherein a non-inverting input of said operational amplifier is connected to an input of said inverter stage via a resistor and is selectively connectable to ground via a switch controlled by said microprocessor; and
an output of said inverter is selectively connectable to said at least one reversing switch.

* * * * *